United States Patent [19]

Akatsu et al.

[11] Patent Number: 5,068,482

[45] Date of Patent: Nov. 26, 1991

[54] METHOD FOR PRODUCING 1,1-DIARYLETHANES

[75] Inventors: Masahiro Akatsu; Hajime Takayama; Takeshi Matsuoka, all of Iwaki, Japan

[73] Assignee: Kureha Kagaku Kogyo K.K., Japan

[21] Appl. No.: 591,172

[22] Filed: Oct. 1, 1990

[30] Foreign Application Priority Data

Oct. 2, 1989 [JP] Japan ................. 1-255202

[51] Int. Cl.$^5$ ..................... C07C 2/72; C07C 2/02
[52] U.S. Cl. ....................... 585/429; 585/426
[58] Field of Search ................. 585/429, 426

[56] References Cited

U.S. PATENT DOCUMENTS 3,714,280  1/1973  Stapp ........................ 585/426

FOREIGN PATENT DOCUMENTS 540207       4/1957   Canada ..................... 585/426
50-4049      1/1975   Japan .
113724       2/1979   Japan ...................... 585/426
61-36499     8/1986   Japan .
63-238028   10/1988   Japan .
50-50004049  1/1975   World Int. Prop. O. .
61-55024145  8/1986   World Int. Prop. O. .

Primary Examiner—Anthony McFarlane
Assistant Examiner—Nhat Phan
Attorney, Agent, or Firm—Lowe, Price, LeBlanc & Becker

[57] ABSTRACT

This invention relates to a method for producing 1,1-diarylethanes expressed by the following general formula (III):

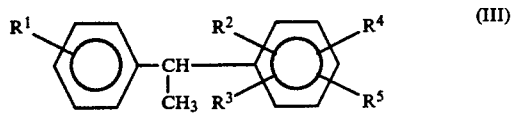

wherein $R^1$-$R^5$ each stand for a hydrogen atom or an alkyl group having 1-3 carbon atoms. This method comprises the reaction of styrenes expressed by the following general formula (I) with an alkylbenzene expressed by the following general formula (II), and is characterized in that the catalyst used is an H-L type zeolite with a $SiO_2/Al_2O_3$ ratio of at least 4, or a zeolite modified by exchanging said H-L type zeolite with a bi- or tri-valent metal ion.

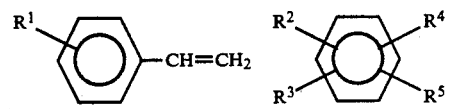

wherein $R^1$-$R^5$ have the same meanings as defined above.

5 Claims, No Drawings

METHOD FOR PRODUCING 1,1-DIARYLETHANES

BACKGROUND OF THE INVENTION

1) Field of the Invention

The present invention relates to a method for producing 1,1-diarylethanes and, more particularly, to a method for producing 1,1-diarylethanes by the reaction of styrene or derivatives thereof (hereinafter referred to as "styrenes") with an alkylbenzene using as a catalyst an HL type zeolite with a $SiO_2/Al_2O_3$ molar ratio of at least 4 or a zeolite obtained by ion-exchanging said HL type zeolite with a di- or tri-valent metal ion.

2) Description of the Related Art

Used as electrical insulating oils, solvents for pressure-sensitive paper purposes, etc., 1,1-diarylethanes have heretofore been prepared by the addition reaction at low temperatures of styrene with an alkylbenzene in the presence of a concentrated sulfuric acid catalyst, as known from Japanese Patent Kokai Publication Nos. 50(1975)-4049. A problem of this addition reaction, however, is that it has to perform the reaction at a low temperature of $-5°$ to $0°$ C. that a cooling medium is needed, and gives to rise an emulsifying phenomenon at neutralizing and water washing steps, which makes the separation of the product difficult. Another problem is that because of using the concentrated sulfuric acid catalyst, a large amount of heavy materials are produced as by-products. Thus, this method is less effective.

It is also known to use Friedel-Crafts catalysts such as aluminium oxide and boron trifluoride for the addition reaction. Incidental to this method, however, are undesired side-reactions such as the polymerization of styrenes, the formation of decomposed products by disproportionation and the occurrence of heavy materials.

In order to eliminate such problems, it has been proposed to prepare diarylalkanes using a solid acid catalyst, as set forth in Japanese Patent Kokai Publication No. 61(1986)-36499. As disclosed there, styrenes are allowed to react with an alkylbenzene at $130°-190°$ C., using as a catalyst a faujasite type of synthetic zeolite ion-exchanged with a lanthanide type rare earth cation. A problem with this technique, however, is that due to the need of rising the reaction temperature to higher than the boiling point of the alkylbenzenes, the reaction system should be pressurized to keep it in a liquid phase, making the reaction equipment expensively.

Japanese Patent Kokai Publication No. 63(1988)-238028 discloses a method for producing diphenylalkanes, using as a catalyst an H-Y type zeolite exchanged with hydrogen ions in which the $SiO_2/Al_2O_3$ molar ratio is at least 4, or its modification exchanged with lanthanide type rare earth cations. This method is carried out at a reaction temperature of $100°-120°$ C. At a reaction temperature below $100°$ C., however, it is not preferable, since the reaction rate is so slow that no sufficiently high conversion and selectivity can be achieved.

As mentioned above, various methods for producing 1,1-diarylethanes have been known in the art. However, the methods using the concentrated sulfuric acid or Friedel-Crafts catalysts can not disolved any problem such as the reaction temperature, by-products, reaction equipment and the like. On the other hand, the method using the solid acid catalyst has to be carried out at a reaction temperature of at least $100°$ C. and a selectivity in this method is not enough.

It is thus desired to develop a method for producing 1,1-diarylethanes under more mild conditions and with a high selectivity.

SUMMARY OF THE INVENTION

It is therefore an object of this invention to provide the method for producing 1,1-diarylethanes at a lower temperature and with a higher selectivity.

As intensive and extensive studies made of how to product 1,1-diarylethanes under more mild conditions and with a higher selectivity to meet such a demand, the inventors have successfully accomplished the present invention.

More specifically, the present invention provides a method for producing 1,1-diarylethanes expressed by the following general formula (III) by the reaction of styrenes expressed by the following general formula (I) with alkylbenzenes expressed by the following general formula (II):

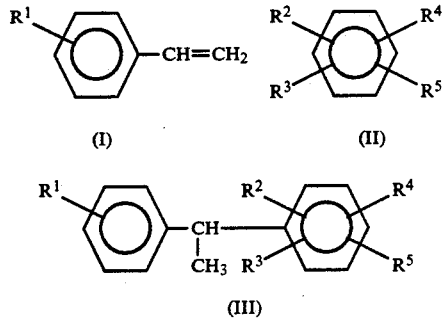

wherein $R^1-R^5$ each stand for a hydrogen atom or an alkyl group having 1-3 carbon atoms, characterized in that:

the catalyst used is an H-L type zeolite with a $SiO_2/Al_2O_3$ molar ratio of at least 4, or a zeolite modified by exchanging said H-L type zeolite with a bi- or tri-valent metal ion.

DETAILED DESCRIPTION OF PREFERRED EMBODIMENTS

The present invention will now be explained in more details.

The styrenes used as one of the starting materials in this invention are expressed by the general formula (I), including aromatic olefins such as styrene, methylstyrene and ethylstyrene by way of example alone.

The alkylbenzenes used as the other starting material are expressed by the general formula (II), including illustratively those having a lower alkyl group such as toluene, xylene, ethylbenzene, isopropylbenzene, diethylbenzene, pseudo-cumene and mesitylene.

The 1,1-diarylethanes produced in this invention are expressed by the general formula (III), including illustratively 1,1-diphenylethane, 1-ethylphenyl-1-phenylethane, 1-phenyl-1-xylylethane, 1-phenyl-1-tolylethane, 1,1-ditolylethane, 1-cumyl-1-tolylethane.

For the synthesis of the 1,1-diarylethanes by the reaction between such styrenes and alkylbenzenes as mentioned above, an H-L type zeolitie with a $SiO_2/Al_2O_3$ molar ratio of at least 4 or a zeolite modified by exchanging said H-L type zeolite with a bi- or tri-valent metal ion (both will hereinafter be generally referred to as the zeolite catalyst) is used as a catalyst. In other words, the zeolite catalysts used in this invention are H-L type zeolites in which alkali metal of K-L type zeolites is exchanged with hydrogen ion and the exchanging ratio is 10% or more, preferably 30% above. Alternatively, use may be made of a variation of the H-L type zeolite in which a part of its hydrogen ions is exchanged to bi- or tri-valent metal ions. For instance, use may preferably be made of a zeolite modified by exchanging the H-L type zeolite with an ion of heavy metals belonging to transition element of the periodic table, such as Cr, Mn, Fe, Co, Ni, Cu, Zn and La, thereby increasing its acid strength. In this case, the ion exchange rate is preferably in a range of 10-90%. It is here noted that the so-called K-L type zeolite, in which the alkali metal is not exchanged with hydrogen ions, is found to be lacking in activity of reaction. At a $SiO_2/Al_2O_3$ molar ratio below 4, the acid strength is low and the catalytic activity is not sufficient, thus making it necessary to raise the reaction temperature. In addition, the selectivity is so low that the formation of oligomers of styrenes is increased.

The zeolite catalysts used in this invention for instance, may be modified in the following procedure. That is, an K-L type zeolite having a $SiO_2/Al_2O_3$ molar ratio of at least 4 and containing an amount of 15-17% in the form of an alkali metal oxide is immersed for ion exchange in an aqueous solution of ammonium chloride or sulfate, thereby decreasing the alkali metal content to about 10% or less, desirously 3% or less. After water washing, the zeolite is calcined at a temperature of 300°-400° C. into an H-L type zeolite in nitrogen gas atmosphere. Then, this H-L type zeolite may be treated with a pH 1.5-5.5 acidic solution of a metal salt capable of producing the aforesaid bi- or tri-valent metal ions, thereby introducing the bi- or tri-valent metal ions into it. Such metal salts, for instance, include cupric chloride, ferrous chloride, ferric chloride, manganese sulfate, chromium chloride, cobalt sulfate, cobalt chloride, nickel chloride and chromium sulfate.

For the reaction between such styrenes and alkylbenzenes as mentioned above using the zeolite catalyst according to this invention, the amounts of the styrenes and alkylbenzenes used should preferably be such that their molar ratio (alkylbenzene/styrene) is 10 or more. An increase in the molar ratio improves the selectivity of 1,1-diarylethanes. A molar ratio below 10 is unpreferred, since the formation of oligomers of styrenes increases with a decrease in the selectivity of 1,1-diarylethanes.

The reaction should preferably be carried out at a reaction temperature of 20° C. or higher, particularly in the range of 25°-100° C. A reaction temperature below 20° C. is unpreferred, because of lowering of reaction rate.

In this invention, no particular limitation is imposed upon how the reaction is carried out. If desired, the reaction may be performed either batchwise or continuously. The reaction time may be 0.5 to 5 hours by selecting the reaction conditions, such reaction form and reaction scale.

It is understood that the end 1,1-diarylethanes can easily be modified with high purity by distillation from the reaction products.

According to this invention, the above-mentioned zeolite catalysts are used to produce 1,1-diarylethanes form styrenes and alkylbenzenes. It is thus possible, i.e., at a reaction temperature lower than the boiling point of the alkylbenzenes, in most cases, at about 30°-80° C. and easily separate the end 1,1-diarylethanes from the reaction solution by distillation.

According to this invention, the reaction of styrenes and alkylbenzenes is performed with a high conversion and a high selectivity with small side products. Accordingly, the 1,1-diarylethanes modified by this invention can be used for electric insulation field or solvent for pressure-sensitive paper.

EXAMPLES

The present invention will now be explained more specifically but not exclusively with reference to the examples.

EXAMPLES 1

A commercially available H-L type zeolite TSZ-500 (with $SiO_2/Al_2O_3$ molar ratio of 6.3, exchanged with 93.5% of hydrogen ions and commercialized by Toso Co., Ltd.) was heat-treated at temperature of 400° C. for 2 hours in a nitrogen gas atmosphere as pre-treatment of the catalyst.

20 g of the catalyst and 341 g of ethylbenzene were set into a separable flask having an inner volume of 500 ml and equipped with a stirrer, a dropping funnel and a thermometer, which were then heated to about 40° C. Thereafter, pre-mixture of 47 g of ethylbenzene and 38 g of styrene was added dropwise through the dropping funnel over 1 hour, followed by a two-hour reaction at a reaction temperature kept at 40°±2° C.

By gas chromatography analysis, the reaction solution was found to be composed of ethylbenzene, styrene, 1-ethylphenyl-1-phenylethane (hereinafter abbreviated as 1,1-EDE), styrene dimer and high-boiling matters. The conversion of styrene and the selectivity of 1,1-EDE were calculated by the following equations:

Styrene conversion = (Starting Amount − Remaining Amount)/Starting Amount 1,1-EDE selectivity = Concentration of 1,1-EDE in Reaction Solution/Total Products; 1,1-EDE, Styrene Dimer and High-Boiling Matters, etc.

The results are shown in Table 1.

EXAMPLE 2

Except that the amount of styrene added was 19 g, Example 1 was repeated to synthesize 1,1-EDE, whose composition was similarly analyzed. The results are shown in Table 1.

EXAMPLE 3

The same H-L type zeolite as used in Ex. 1 was immersed for cupric ion exchange in an aqueous solution of cupric chloride to perform exchanging at an exchange rate of 40% and heat-treated at 400° C. for 2 hours in a nitrogen gas atmosphere. The same procedure as in Ex. 1 was carried out to synthesize 1,1-EDE, whose composition was similarly analyzed. The results are shown in Table 1.

EXAMPLES 4-9

The H-L type zeolites were exchanged with Ni, Cr, Co, Zn, Fe or Mn ions in place of cupric ions. The same procedure as explained in Ex. 3 was carried out in Ex. 4-9 to synthesize 1,1-EDE, whose composition was similarly analyzed. The results are shown in Table 1.

COMPARATIVE EXAMPLE 1

The same procedure as in Ex. 1 was carried out except that an H-L type zeolite wherein $SiO_2/Al_2O_3 = 3.5$ was used as a catalyst to synthesize 1,1-EDE, whose composition was similarly analyzed. The results are shown in Table 1.

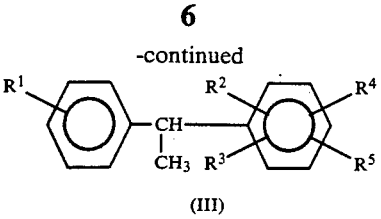

(III)

wherein $R^1$-$R^5$ each stand for a hydrogen atom or an alkyl group having 1-3 carbon atoms, the improvement comprising using a catalyst which is zeolite L in H form with a $SiO_2/Al_2O_3$ molar ratio of at least 4, or a zeolite modified by exchanging said zeolite L in H form with a bi- or tri-valent metal ion.

TABLE 1

|  | Example 1 | Example 2 | Example 3 | Example 4 | Example 5 | Example 6 | Example 7 | Example 8 | Example 9 | Comp. Ex. 1 |
|---|---|---|---|---|---|---|---|---|---|---|
| Type | HL type | HL type | HL type | HL type | HL type | HL type | HL type | HL type | HL type | HL type |
| Cation exchange | — | — | Cu 40% | Ni 40% | Cr 40% | Co 40% | Zn 40% | Fe 40% | Mn 40% | — |
| $SiO_2/Al_2O_3$ | 6.3 | 6.3 | 6.3 | 6.3 | 6.3 | 6.3 | 6.3 | 6.3 | 6.3 | 3.5 |
|  | TSZ-500 | TSZ-500 | TSZ-500 | TSZ-500 | TSZ-500 | TSZ-500 | TSZ-500 | TSZ-500 | TSZ-500 |  |
| Ethyl benzene | 86.22 wt % | 94.44 wt % | 86.11 wt % | 86.18 wt % | 86.17 wt % | 86.21 wt % | 86.18 wt % | 86.14 wt % | 86.26 wt % | 91.39 |
| Styrene | 0.00 | 0.00 | 0.00 | 0.00 | 0.00 | 0.00 | 0.00 | 0.00 | 0.00 | 5.35 |
| 1,1-EDE | 11.63 | 5.07 | 12.96 | 12.88 | 12.90 | 12.84 | 12.85 | 12.86 | 12.78 | 2.62 |
| Styrene dimer | 1.10 | 0.31 | 0.83 | 0.84 | 0.83 | 0.82 | 0.82 | 0.81 | 0.84 | 0.12 |
| High-boiling matters | 1.05 | 0.18 | 0.10 | 0.10 | 0.10 | 0.13 | 0.15 | 0.19 | 0.12 | 0.58 |
| Conversion | 1.0000 | 1.0000 | 1.0000 | 1.0000 | 1.0000 | 1.0000 | 1.0000 | 1.0000 | 1.0000 | 0.4535 |
| Selectivity | 0.8439 | 0.9119 | 0.9330 | 0.9320 | 0.9326 | 0.9311 | 0.9298 | 0.9280 | 0.9300 | 0.7892 |

What is claimed is:

1. In a method for producing 1,1-diarylethanes expressed by the following general formula (III) by the reaction of styrenes expressed by the following general formula (I) with alkylbenzenes expressed by the following general formula (II):

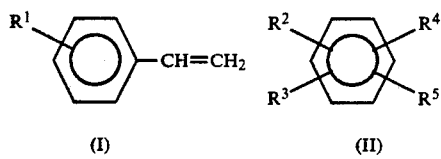

(I)　　　　　　　(II)

2. A method as claimed in claim 1, wherein the 1,1-diarylethanes are 1-ethylphenyl-1-phenylethane derivatives having the following formula:

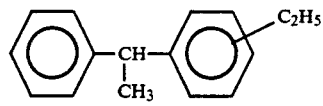

3. A method as claimed in claim 1, wherein the bi- or tri-valent metal ion is a cation of a metal selected from the group consisting of Cu, Ni, Cr, Co, Zn, Fe or Mn.

4. A method as claimed in claim 1, wherein the bi- or tri-valent metal ion is a cation selected from lanthanide metals.

5. A method as claimed in claim 1, wherein said starting materials of formulae (II) and (I) have a molar alkylbenzene/styrene ratio of 10 or more.

* * * * *